United States Patent [19]

Oxford et al.

[11] 4,316,907

[45] Feb. 23, 1982

[54] HETEROCYCLIC COMPOUNDS, PROCESSES FOR THEIR PREPARATION AND THEIR USE

[75] Inventors: Alexander W. Oxford, Royston; John Bradshaw, Dane End, near Ware; Ian H. Coates, Hertford, all of England

[73] Assignee: Glaxo Group Limited, London, England

[21] Appl. No.: 163,568

[22] Filed: Jun. 27, 1980

[30] Foreign Application Priority Data

Jun. 29, 1979 [GB] United Kingdom ............... 22736/79

[51] Int. Cl.³ ..................... A61K 31/38; C07D 333/24
[52] U.S. Cl. ..................................... 424/275; 549/60; 549/72
[58] Field of Search ..................... 549/72, 60; 424/275

[56] References Cited

U.S. PATENT DOCUMENTS 4,024,156 5/1977 Bagli et al. .
4,082,772 4/1978 Bagli et al. .
4,085,221 4/1978 Smith ................................. 424/275
4,086,357 4/1978 Large ................................. 424/275

FOREIGN PATENT DOCUMENTS 2026474 2/1980 United Kingdom .

Primary Examiner—Alan Siegel

Attorney, Agent, or Firm—Bacon & Thomas

[57] ABSTRACT

Thiophene carboxamides are described of general formula I

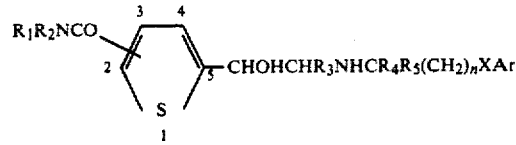

in which the amide function is in the 2- or 3-position on the thiophene ring, $R_1$ to $R_5$ inclusive are hydrogen atoms or lower alkyl groups, X is $-CH_2-$, $-O-$ or $-NR_6-$ where $R_6$ is hydrogen or a lower alkyl group, n is a number from 0 to 3 and Ar is an optionally substituted phenyl group and their physiologically acceptable salts.

The compounds have been found to lower blood pressure in animals and to exhibit a blocking action at $\beta$-adrenoreceptors and their use is indicated for the treatment of cardiovascular disorders such as hypertension and angina. Some of the compounds also exhibit a blocking action on $\alpha$-adrenoreceptors and their use is indicated for the treatment of hypertention.

16 Claims, No Drawings

HETEROCYCLIC COMPOUNDS, PROCESSES FOR THEIR PREPARATION AND THEIR USE

This invention relates to heterocyclic compounds, to processes for their preparation, to pharmaceutical compositions containing them and to their medical use.

The present invention provides a thiophene-carboxamide of general formula (I):

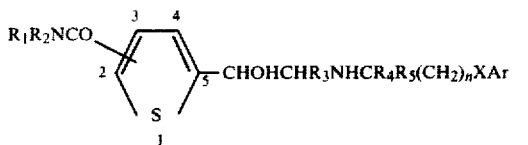

in which the amide function is in the 2 or 3 position on the thiophene ring, and wherein $R_1$, $R_2$, $R_3$, $R_4$ and $R_5$, which may be the same or different, each represents a hydrogen atom or a lower alkyl group;

X represents $-CH_2-$, $-O-$ or $-NR_6-$ where $R_6$ represents a hydrogen atom or a lower alkyl group;

n is a number from zero to 3, with the proviso that when n is zero X cannot represent $-O-$ or $-NR_6-$;

Ar represents a phenyl group optionally substituted by one or more substituents selected from halogen atoms, $C_1-C_3$ alkyl groups, phenyl groups and the groups $-OR_7$ or amino groups ($-NR_8R_9$) in which $R_7$ and $R_8$ and $R_9$ independently represent a hydrogen atom or a $C_1-C_3$ alkyl group or an alkylenedioxy group of formula $-O(CH_2)_mO-$ where m is 1 or 2 and physiologically acceptable salts thereof.

The compounds according to the invention include all optical isomers and mixtures thereof.

With reference to the general formula (I), the lower alkyl group represented by $R_1$ to $R_6$ inclusive may be a straight-chain or branched-chain alkyl group preferably containing 1 to 4 carbon atoms.

In the general formula (I) the groups represented by $R_1$ to $R_6$ inclusive are preferably hydrogen or methyl groups.

In particular, a preferred class of compounds of general formula (I) comprises those compounds wherein $R_1$, $R_2$, $R_3$, $R_4$ and $R_5$ are selected from hydrogen atoms or methyl groups, X represents $-CH_2-$, $-O-$ or $-N$ methyl, n is 1, Ar represents phenyl optionally substituted by fluorine, one or more methyl groups, phenyl, dimethylamino or methylenedioxy groups.

A particularly preferred class of compounds of general formula (I) includes those compounds wherein $R_1$, $R_2$, $R_3$ and $R_4$ are hydrogen atoms, $R_5$ is a methyl group, n is 1, X is $-CH_2-$ and Ar represents a phenyl group or phenyl group substituted by a fluorine atom, or a dimethylamino, phenyl or methylenedioxy group.

Particularly preferred compounds falling within this class include:

5-[1-Hydroxy-2-[(1-methyl-3-phenylpropyl)amino]ethyl]thiophene-3-carboxamide;

5-[1-Hydroxy-2-[(1-methyl-3-phenylpropyl)amino]ethyl]thiophene-2-carboxamide;

5-[1-Hydroxy-2-[[3-(4-fluorophenyl)-1-methylpropyl]amino]ethyl]thiophene-3-carboxamide;

5-[2-[[3-(1,3-Benzodioxol-5-yl)-1-methylpropyl]amino]-1-hydroxyethyl]thiophene-3-carboxamide;

5-[2-[[3-[(1.1'-Biphenyl)-4-yl]-1-methylpropyl]amino]-1-hydroxyethyl]thiophene-3-carboxamide;

5-[2-[[3-[4-(Dimethylamino)phenyl]-1-methylpropyl]amino]-1-hydroxyethyl]thiophene-3-carboxamide and salts and hydrated forms thereof.

Suitable physiologically acceptable salts of the compounds of the general formula (I) are acid addition salts formed with organic or inorganic acids, for example, hydrochloride, tartrate maleate, fumarate and citrate.

The compounds according to the invention have been found to lower blood pressure in animals and to exhibit a blocking action at $\beta$-adrenoreceptors as shown by their ability to antagonise the cardiovascular effects of isoprenaline in anaesthetised dogs. Thus the compounds are useful for treating cardiovascular disorders such as hypertension and angina.

Some of the compounds of the invention also exhibit a blocking action on $\alpha$-adrenoreceptors, as shown by their ability to antagonise the pressor effects of phenylephrine in anaesthetised dogs at doses at which they also block $\beta$-adrenoreceptors. Such compounds are particularly useful for the treatment of both mild and severe hypertension. They may also be useful in the treatment of glaucoma and peripheral vascular diseases, for example Raynaud's disease.

The blocking actions on the $\alpha$- and $\beta$-adrenoreceptors were demonstrated in the bilaterally vagotomised anaesthetised dog. The experimental techniques were identical to those described by Farmer et al in Brit. J. Pharmacol. 45 No. 4, pages 660–675 (1972) except that the $\alpha$-agonist used was phenylephrine and not noradrenaline or oxymetazoline as in the article referred to.

The $\beta$-blocking activities of the compounds were determined from their ability to antagonise increases in heart rate and decreases in blood pressure induced by intravenous ($-$)isoprenaline; from the results obtained, $DR_{10}$ values were calculated for each antagonist. The $DR_{10}$ value is the dose of antagonist required to produce a 10-fold shift to the right of the agonist dose-response curve for increases in heat rate or decreases in blood pressure.

The $\alpha$-blocking activity of the compounds was determined from their ability to prevent increases in diastolic blood pressure induced by intravenous phenylephrine. The $\alpha$-blocking activity was quantified as a $DR_{10}$ value as described above.

The compounds according to the invention may be formulated for use in human or veterinary medicine for therapeutic or prophylactic purposes.

Accordingly, the invention also provides a pharmaceutical composition which comprises at least one compound of the general formula (I) or a physiologically acceptable salt thereof together with a physiologically acceptable excipient or carrier therefor.

Such compositions may be presented for use in a conventional manner with other active ingredients if required.

Thus the compounds according to the invention may be formulated for oral, buccal, topical, parenteral or rectal administration and may also be formulated as eye drops for ophthalmic administration. Oral administration is preferred.

For oral administration, the pharmaceutical composition may take the form of, for example, tablets, capsules, powders, solutions, syrups or suspensions prepared by conventional means with physiologically acceptable excipients. For buccal administration the composition may take the form of tablets or lozenges formulated in conventional manner.

The compounds of the invention may be formulated for parenteral administration by bolus injection or by continuous infusion. Formulations for injection may be presented in unit dosage form in ampoules, or in multi-dose containers, with or without an added preservative. The composition may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

The doses of the active ingredient which may be used may vary within a wide range depending upon the severity of the condition being treated. In general a dosage, either orally or intravenously may be from 20 to 800 mg, preferably 50 to 400 mg, given from once to four times per day but a total daily dose may be up to 2 g.

The compounds according to the invention may be prepared by a number of processes.

For example, a compound of general formula (I) may be obtained from a precursor of general formula (II):

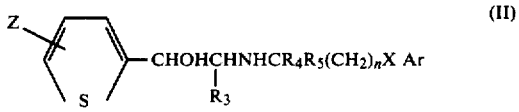

(II)

wherein $R_3$, $R_4$, $R_5$, n, X and Ar are as previously defined and Z is a nitrile group or a group of formula $-CO_2R_{10}$ where $R_{10}$ represents a hydrogen atom, a $C_1-C_4$ alkyl, or an aryl or an aralkyl group by conventional procedures such as, where Z is an ester group by reaction with a compound of formula $R_1R_2NH$ optionally in the presence of a solvent, where Z is a carboxylic acid group, by conversion into an activated derivative, for example an acid halide, which is then treated with a compound of formula $R_1R_2NH$ optionally in a suitable solvent or, alternatively, the acid may be treated with a compound of formula $R_1R_2NH$ in the presence of a coupling agent, for example dicyclohexylcarbodiimide preferably in the presence of a solvent; and where Z is a nitrile group, by hydrolysis for example with aqueous acid or alkali, or by treatment with an ion exchange resin such as Amberlite IRA 400 which provides compounds wherein $R_1$ and $R_2$ are hydrogen atoms.

A compound of general formula (I) may also be obtained from an amine of the general formula (III);

(III)

where $R_4$, $R_5$, n, X and Ar are as previously defined and $R_{11}$ is a hydrogen atom or a protecting group which may be removed by hydrogenolysis to yield a hydrogen atom, for example a benzyl group.

Thus, an amine of general formula (III) may be reacted with (a) a halohydrin of general formula (IV):

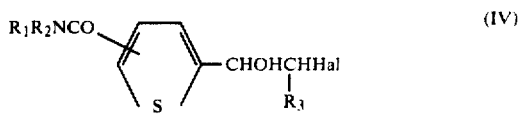

(IV)

or with (b) an oxirane of general formula (V):

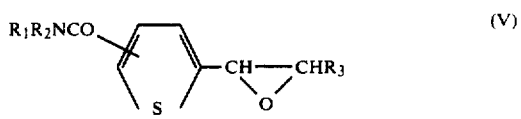

(V)

where $R_1$, $R_2$ and $R_3$ are as previously defined and Hal represents a halogen atom e.g. chlorine, bromine or iodine.

The reaction (a) of the amine with the halohydrin may optionally be carried out in the presence of a solvent, for example dimethylformamide or an alcohol such as isopropanol at a temperature preferably between 20° C. and 180° C. If desired the reaction may be performed in the presence of an alkali metal halide such as sodium iodide.

Where $R_{11}$ in the amine of general formula (III) is a protecting group, for example benzyl, it may be removed by hydrogenolysis in the presence of a metal catalyst to give the desired compound of general formula (I).

The halohydrin of general formula (IV) may be prepared from a corresponding haloketone of general formula (VI):

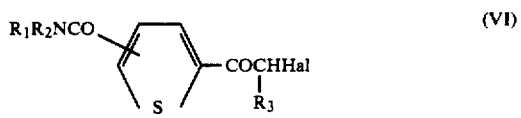

(VI)

where $R_1$, $R_2$, $R_3$ and Hal are as previously defined by reduction using, for example, sodium borohydride in an alcohol.

The haloketone of general formula (VI) may be prepared from the corresponding ketone by standard halogenation reactions, for example, by treatment with a halogen, such as bromine, in a solvent, for example chloroform.

The oxirane of general formula (V) may be prepared from a thiophenehalohydrin of general formula (IV) as previously defined by dehydrohalogenation under basic conditions, for example, in the presence of triethylamine.

The compounds of general formula (I) may also be prepared by reduction of a ketone or an imine followed, if necessary, by removal of the protecting group, $R_{11}$.

For example, a ketone of general formula (VII):

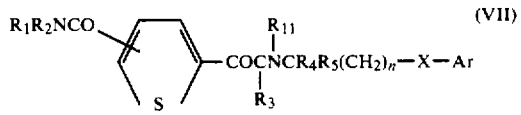

(VII)

or an imine of general formula (VIII):

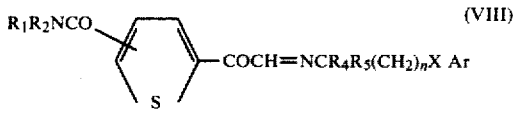

wherein $R_1$, $R_2$, $R_3$, $R_4$, $R_5$, $R_{11}$, X, n and Ar are as previously defined,
may be reduced to give a compound of general formula (I).

The reduction may be carried out with, for example, a complex metal hydride, generally in the presence of a solvent, such as sodium borohydride in ethanol or methanol.

The ketone of general formula (VII) may be prepared by reaction of a haloketone of general formula (VI) as previously defined with an amine of the general formula (III), followed, where necessary, by removal of the protecting group $R_{11}$. The reaction may optionally be performed in the presence of a solvent such as acetone, butanone, dimethylformamide or ethanol, and generally at a temperature of 20° C. to reflux.

The imine of general formula (VIII) may be prepared by reaction of a glyoxal of general formula (IX):

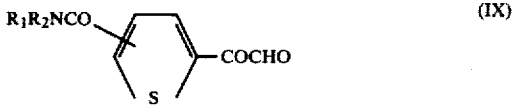

where $R_1$ and $R_2$ are as previously defined, with an amine of general formula (III), in which $R_{11}$ is a hydrogen atom, preferably in a solvent, for example benzene or ethanol at an elevated temperature.

A glyoxal of formula (IX) may be prepared, for example by treating a dihaloketone of general formula (X):

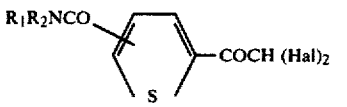

wherein $R_1$, $R_2$ and Hal are as previously defined with alkali.

Another possibility for the preparation of the compounds (I) is by reductive alkylation of a primary amine. For example, an amine of general formula (XI):

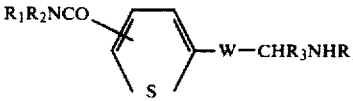

wherein $R_1$ and $R_2$ are as previously defined, W represents the group

or the group $>C=0$ and $R_{12}$ represents a hydrogen atom or a group removable by hydrogenolysis to give a hydrogen atom, for example a benzyl group, may be treated with a compound of general formula (XII):

$$ArX(CH_2)_nCOR_4 \qquad (XII)$$

where Ar, X and n are as previously defined and $R_4$ is a hydrogen atom or an alkyl group
in the presence of a complex metal hydride such as sodium cyanoborohydride.

Where $R_{12}$ is a hydrogen atom the amine of formula (XI) may be treated with a compound of formula (XII) followed by reduction in the presence of a complex metal hydride such as sodium borohydride or sodium cyanoborohydride in an alcohol.

The primary amine of general formula (XI) where $R_{12}$ represents a hydrogen atom may be prepared by reacting a halide of formula (XIII):

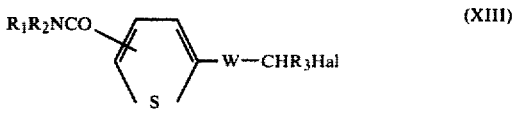

where $R_1$, $R_2$, $R_3$, W and Hal are as previously defined with hexamethylenetetramine in a solvent, for example chloroform, at a temperature from ambient to the reflux, followed by hydrolysis of the resulting salt with a concentrated mineral acid such as hydrochloric or sulphuric acid, optionally in a solvent, for example ethanol. Where W represents the group $>C=0$ the hexamine quaternary salt may be reduced prior to hydrolysis by for example a complex metal hydride such as sodium borohydride in ethanol.

In the above reactions, the group $R_1R_2NCO-$ may be replaced by a group convertible thereto which is, for example, a nitrile group or a group of formula $-CO_2R_{10}$ (where $R_{10}$ represents a hydrogen atom, a $C_1-C_4$ alkyl, an aryl or an aralkyl group) by conventional procedures such as those previously indicated.

The compounds of general formula (I) may be isolated as such or in the form of a salt, preferably a physiologically acceptable salt thereof. Salts of formula (I) may be prepared by conventional means, for example by treatment of the free base with an appropriate acid such as ethereal hydrogen chloride in a suitable solvent such as ether.

The invention is illustrated by the following Examples—Temperatures are in °C.:

EXAMPLE 1

5-[1-Hydroxy-2-[(1-methyl-3-phenylpropyl)amino]ethyl]thiophene-3-carboxamide hydrochloride (a) 5-Acetylthiophene-3-carboxamide A solution of aluminium chloride (66.5 g) in acetyl chloride (200 ml) was stirred at room temperature for 1 h. Thiophene-3-carboxamide (12.7 g) was added in one aliquot and the resulting pale yellow solution stirred at room temperature for 4 h before being added cautiously to ice (1 kg) and dilute hydrochloric acid (400 ml). The resulting solution was saturated with sodium chloride and extracted with butanone (6×500 ml) and then ethyl acetate (6×500 ml). The combined organic extracts were evaporated to small volume, diluted with ethyl acetate (1000 ml) and washed thoroughly with sodium carbonate solution (6×100 ml) and water (100 ml) and then dried and evaporated to small volume to deposit the title compound as a white crystalline solid (14.0 g)

m.p. 156°–157° which recrystallised from ethyl acetate, m.p. 156°–158°.

(b) 5-(Bromoacetyl)thiophene-3-carboxamide

A solution of 5-acetylthiophene-3-carboxamide (0.5 g) in chloroform at 50° was treated with hydrogen bromide in acetic acid (4 drops) and then bromine (0.15 ml) in chloroform (10 ml) dropwise over 30 min. The resulting pale yellow solution was washed with water (2×100 ml), dried and evaporated to small volume to deposit the title compound as a white solid (0.55 g) which recrystallised from water, m.p. 150°–157° (d).

(c) 5-[1-Hydroxy-2-[(1-methyl-3-phenylpropyl)amino]ethyl]thiophene-3-carboxamide hydrochloride An ice-cold solution of 5-(bromoacetyl) thiophene-3-carboxamide (4.0 g) in methanol (70 ml) was treated with sodium borohydride (1.9 g) in portions over 30 min., then stirred in an ice bath for a further 2 h. The solution was poured into icewater (200 ml), saturated with sodium chloride and extracted with ethyl acetate (4×200 ml). The extract was dried and evaporated to dryness to give a white foam which was used without further purification. The foam was treated with 1-methylbenzenepropanamine (8.0 g) and the resulting mobile oil was heated on a steam bath for 2 h. The resulting dark brown oil was dissolved in ethyl acetate (20 ml) and added dropwise to stirred petroleum ether (b.p. 60°–80°, 400 ml), to precipitate a brown gum which was partially purified on a silica column (Kieselgel 60,260 g) eluted with ethyl acetate/methanol/ammonia (95:5:0:1). The resulting pale brown gum was further purified on a silica column (Kieselgel 60,100 g) eluted with toluene/ethanol/ammonia (100:20:1) to give a buff-coloured foam (0.7 g). This foam was dissolved in dry ether and treated with ethereal hydrogen chloride to precipitate the title hydrochloride as an off-white amorphous solid (0.65 g) m.p. 75°–85°.

Found: C,56.06; H,7.0; N,7.6; $C_{17}H_{22}N_2O_2S.HCl.\frac{1}{2}H_2O$ requires C,56.1; H,6.6; N,7.7%.

EXAMPLE 2

5-[1-Hydroxy-2-](1-methyl-3-phenylpropyl)amino]ethyl]thiophene-2-carboxamide hemihydrate

(a) 5-Acetylthiophene-2-carboxamide

A mixture of 5-acetylthiophene-2-carboxylic acid (5.6 g) and thionyl chloride (5.25 ml) in benzene (70 ml) was refluxed for 3 h; a further portion of thionyl chloride (5.3 ml) was added and reflux continued for 1.5 h. The resulting solution was evaporated to leave a white solid which was dissolved in tetrahydrofuran (70 ml). Aqueous ammonia (s.g. 0.88; 6 ml) was added and the reaction mixture was stirred for 1 h. The white precipitate was washed with water, leaving the title amide (3.43 g) mp 231°–233°. TLC SiO₂ (EtOAc) Rf 0.28.

(b) 5-(Bromoacetyl)thiophene-2-carboxamide

A solution of bromine (0.86 ml) in chloroform (100 ml) was added to a suspension of 5-acetylthiophene-2-carboxamide (2.94 g) in refluxing chloroform (500 ml) containing six drops of hydrogen bromide in acetic acid. After 30 min, the mixture was cooled and filtered, giving the title bromoketone (3.9 g) as a white solid. TLC SiO₂ (EtOAc) RF 0.34.

(c) 5-[1-Hydroxy-2-[(1-methyl-3-phenylpropyl)amino]ethyl]thiophene-2-carboxamide, hemihydrate Sodium borohydride (3.2 g) was added in portions to an ice-cold, stirred suspension of the bromoketone (3.8 g) in methanol (200 ml). The resulting solution was stirred for 10 min., poured into iced water (500 ml) and extracted with ethyl acetate (3×200 ml). Evaporation of the dried (MgSO₄) extract gave a yellow solid which was dissolved in isopropanol (600 ml) and 1-methylbenzenepropanamine (4.4 g), and refluxed for 17 h. The solvent was evaporated and the resulting oil was partitioned between ethyl acetate (2×200 ml) and sodium bicarbonate (2 M, 200 ml). The dried (MgSO₄) organic phase was evaporated to leave a brown oil which was twice purified by chromatography on silica (Kieselgel 60, 150 g) eluted with ethyl acetate-methanol-ammonia (ca. 20:1:0.1) to give the title compound as a pale yellow solid (0.1 g) m.p. 108°–116°. TLC SiO₂ (EtOAc:-MeOH:NH₃aq.–4:1:4 drops) Rf 0.31.

EXAMPLE 3

5-[1-Hydroxy-2-[(3-phenylpropyl)amino]ethyl]thiophene-3-carboxamide

An ice-cold solution of 5-(bromoacetyl) thiophene-3-carboxamide (1.0 g) in methanol (30 ml) was treated with sodium borohydride (0.76 g). The resulting solution was stirred for 1 h, poured into ice (ca. 200 g), saturated with sodium chloride and extracted with ethyl acetate (3×300 ml). The dried (MgSO₄) extract was evaporated to yield a colourless oil (1.0 g) which was dissolved in 3-phenyl-1-propylamine (1.62 g) and stirred with potassium iodide (0.66 g) for 3 h at room temperature. The reaction mixture was partitioned between ethyl acetate (800 ml) and dilute aqueous sodium bicarbonate (0.8%, 2×150 ml), and the organic phase dried (MgSO₄), evaporated to ca. 7 ml, and added to light petroleum (b.p. 60°–80°; 400 ml) to precipitate a brown gum (2.0 g). Cooling to 0° and trituration with ethylacetate gave a white solid (0.3 g). This was recrystallised from isopropyl acetate to yield the title compound as fine white crystals (0.25 g) m.p. 112°–114°. TLC SiO₂ (EtOAc/MeOH/NH₄OH-4:1:0.1) Rf 0.3.

EXAMPLE 4

5-[1-Hydroxy-2-[(1,1-dimethyl-3-phenylpropyl)amino]ethyl]thiophene-3-carboxamide 1,1-Dimethyl-3-phenylpropylamine hydrochloride (1.7 g) was partitioned between ethyl acetate (400 ml) and aqueous sodium bicarbonate (8%, 100 ml). The organic phase was dried (MgSO₄) and evaporated to give a pale yellow oil (1.4 g) which was stirred with a solution of 5-(bromoacetyl) thiophene-3-carboxamide (1.0 g) in butanone (75 ml) for 7 h and clarified by filtration. The filtrate was evaporated to yield a brown gum, which was dissolved in methanol (50 ml), treated with sodium borohydride (0.76 g) for 0.75 h, poured into water (200 ml), acidified with 2N hydrochloric acid, neutralised with aqueous sodium bicarbonate (8%), and extracted with ethyl acetate (3×200 ml). The dried (MgSO₄) extract was evaporated to ca. 30 ml and added to vigorously stirred light petroleum (b.p. 60°–80°; 500 ml) to precipitate a sticky white solid (1.0 g), which was washed with light petroleum (b.p. 60°–80°; 50 ml) and recrystallised from ethyl acetate to give the title compound as a white crystalline solid (0.46 g) m.p.

175°–177°. TLC (EtOAc-2% MeOH-10% NH₄OH) Rf 0.13.

EXAMPLE 5

5-[1-Hydroxy-2-[(1-methyl-3-phenylpropyl)amino]ethyl]-N,N-dimethylthiophene-2-carboxamide (a) 5-Acetyl-N,N-dimethylthiophene-2-carboxamide A solution of 5-acetylthiophene-2-carboxylic acid (1.70 g) in thionyl chloride (50 ml) was refluxed for 30 min., cooled, and evaoporated to leave a yellow solid, which was treated with aqueous dimethylamine (30%; 15 ml), stirred for 1 h, and then heated until a solution was obtained. The reaction mixture was cooled, acidified with hydrochloric acid (2 M; ca. 50 ml), and extracted with ethyl acetate (3×100 ml). The extract was washed with aqueous sodium bicarbonate (1 M, 2×100 ml) and water (50 ml), dried, and evaporated to leave a yellow solid (1.57 g) which was recrystallised from diethyl ether to give the title amide as a yellow solid (1.34 g), m.p. 110°–112°. TLC SiO₂ (EtOAc) Rf 0.22.

(b) 5-(Bromoacetyl)-N,N-dimethylthiophene-2-carboxamide

A solution of bromine (0.68 ml) in chloroform (10 ml) was added dropwise to a solution of 5-acetyl-N,N-dimethyl-2-thiophenecarboxamide (2.44 g) in refluxing chloroform (50 ml) containing hydrogen bromide in acetic acid (6 drops). After 30 min the solution was cooled and partitioned between aqueous sodium bicarbonate (1 M; 100 ml) and chloroform (2×100 ml). The dried (MgSO₄) organic phase was evaporated to leave a light brown solid (3.5 g) which was recrystallised from toluene to give the title compound as a beige solid (2.9 g). TLC SiO₂ (EtOAc) Rf 0.29.

(c) 5-[1-Hydroxy-2-[(1-methyl-3-phenylpropyl)amino]ethyl]-N,N-dimethylthiophene-2-carboxamide Sodium borohydride (2.0 g) was added to an ice-cold suspension of the bromoketone (2.66 g) in methanol (200 ml). After 10 min the solution was added to brine (500 ml) and extracted with ethyl acetate (3×200 ml). The dried (MgSO₄) organic extract was evaporated to leave a yellow oil which was refluxed with 1-methyl-3-phenylpropylamine (3 ml) in isopropanol (250 ml) for 18 h, and partitioned between water (500 ml) and ethyl acetate (3×200 ml). The dried (MgSO₄) extract was evaporated to leave a brown oil which was purified on a short path silica column (200 g) eluted with ethyl acetate/isopropanol/triethylamine (80:20:1). The appropriate fractions were combined, evaporated, dissolved in ethyl acetate (20 ml) and diethyl ether (30 ml), and treated with ethereal citric acid to precipitate the title compound as a hygroscopic cream citrate (0.86 g) m.p. 71°–77°. TLC SiO₂ (EtOAc/MeOH/NH₃ aq-4:1:4 drops) Rf 0.26.

EXAMPLE 6

5-[-Hydroxy-2-[(1-methyl-2-phenoxyethyl)amino]ethyl]thiophene-3-carboxamide, hydrate (1:0:3)

Sodium borohydride (1.9 g) was added portionwise to an ice-cold stirred suspension of 5-(bromoacetyl)thiophene-3-carboxamide (2.6 g) in methanol (100 ml). After 30 min the solution was added to iced brine (250 ml) and extracted with ethyl acetate (4×100 ml). The dried (MgSO₄) extract was evaporated, treated with 1-methyl-2-phenoxyethylamine (4.5 g) at 80° for 4 h, and partitioned between ethyl acetate (3×200 ml) and water (200 ml). The organic phase was washed with aqueous sodium bicarbonate (1 M; 100 ml), dried (MgSO₄) and evaporated to leave a brown oil.

A solution of the crude product in methanol (10 ml) was added dropwise to stirred light petroleum (bp 60°–80°:200 ml) to precipitate a brown oil. This procedure was repeated and the product was then stirred with dry diethyl ether. The resulting light brown solid was further purified by chromatography on a silica column (50 g) eluted with ethyl acetate/20% methanol/1% ammonia and then a silica column (40 g) eluted with chloroform/15% methanol, giving the title compound as a light brown solid (0.62 g) m.p. 137.5°–141.5°. TLC SiO₂ (EtOAc/MeOH/NH₃ aq-4:1:4 drops) Rf 0.26.

EXAMPLE 7

5-[1-Hydroxy-2-[[3-(4-fluorophenyl)-1-methylpropyl]amino]ethyl]thiophene-3-carboxamide, hydrate (1:0:3)

Sodium borohydride (1.9 g) was added portionwise to an ice-cold stirred suspension of 5-(bromoacetyl)thiophene-3-carboxamide (2.6 g) in methanol (100 ml). After 30 min, the solution was added to iced brine (250 ml) and extracted with ethyl acetate (4×100 ml). The dried (MgSO₄) extract was evaporated, treated with 3-(4-fluorophenyl)-1-methylpropylamine (5.0 ) at 80° for 4.5 h, and partitioned between ethyl acetate (3×200 ml) and water (200 ml). The organic phase was washed with aqueous sodium bicarbonate (1 M; 100 ml), dried (MgSO₄) and evaporated to leave a brown oil.

A solution of the crude product in methanol (1 ml) and ethyl acetate (10 ml) was added dropwise to stirred light petroleum (bp 60°–80°:200 ml) to precipitate a greasy brown solid. This procedure was repeated and the product was then stirred with dry diethyl ether (200 ml). The resulting yellow powder was further purified on a silica column eluted with ethyl acetate/20% methanol giving a yellow oil, which on trituration with diethyl ether gave the title compound as a light brown solid (0.32 g), m.p. 134.5°–140°. TLC SiO₂ (EtOAc/MeOH/NH₃ aq-4:1:4 drops) Rf 0.21.

EXAMPLE 8

5-[1-Hydroxy-2-[(1-methyl-3-phenylpropyl)amino]ethyl]-N,N-dimethylthiophene-3-carboxamide, compound with fumaric acid and water (1:0:5:2)

(a) 5-(Bromoacetyl)-N,N-dimethylthiophene-3-carboxamide

A solution of bromine (1.08 ml) in chloroform (5 ml) was added dropwise to a solution of the ketone (3.8 g) in chloroform (100 ml) containing four drops of hydrogen bromide in acetic acid. The reaction mixture was stirred at room temperature for 1 h, heated to 50°, cooled, washed with water (100 ml), aqueous sodium bicarbonate (1 M; 100 ml), and brine (100 ml): dried, and evaporated to give a white solid (5.12 g). TLC SiO₂ (EtOAc) Rf 0.24.

(b)
5-[1-Hydroxy-2-[(1-methyl-3-phenylpropyl)amino]ethyl]-N,N-dimethylthiophene-3-carboxamide, compound with fumaric acid and water (1:0.5:2)

Sodium borohydride (1.9 g) was added portionwise to an ice-cold, stirred solution of the bromoketone (3.3 g) in methanol (100 ml). After 20 min, the reaction mixture was added to brine (150 ml), acidified with hydrochloric acid (2 M), stirred for 20 min, basified with aqueous sodium bicarbonate (1 M), and extracted with ethyl acetate (4×100 ml). The dried (MgSO₄) extract was evaporated to leave a yellow oil which was treated with 1- methyl-3-phenyl-propylamine (4.5 g) at 50° for 18 h and partitioned between aqueous sodium bicarbonate (1 M; 100 ml) and ethyl acetate (3×100 ml). The dried (MgSO₄) organic phase was evaporated, dissolved in diethyl ether (10 ml) and added to light petroleum (b.p. 60°-80°; 200 ml) to precipitate a brown gum (3.0 g) which was purified on a silica (Merck 7734; 60 g) column eluted with ethyl acetate/20% methanol/1% ammonia. The appropriate fractions (Rf 0.35) were evaporated dissolved in ethyl acetate (25 ml) and diethyl ether (25 ml), and treated with excess ethereal fumaric acid to precipitate the title compound as a light brown, hygroscopic solid (0.71 g), m.p. 63°–66°. TLC (base) SiO₂ (EtOAc/20% MeOH/1%NH₃aq.) R$_f$ 0.35.

EXAMPLE 9

5[2-[[2-(2,6-Dimethylphenoxy)-1-methylethyl]amino]-1-hydroxyethyl]thiophene-3-carboxamide (a)
5-(2-Amino-1-hydroxyethyl)thiophene-3-carboxamide A solution of hexamethylenetetramine (3.5 g) in chloroform (75 ml) was added dropwise to an ice-cold, stirred suspension of 5-(bromoacetyl)thiophene-3-carboxamide (6.20 g) in chloroform (50 ml), stirred at room temperature for 20 h, and filtered to give a white solid (10.3 g).

Sodium borohydride (1.9 g) was added portionwise to an ice-cold, stirred suspension of this quaternary salt (10.3 g) in ethanol (250 ml). The reaction mixture was stirred for 15 min at 0° and 30 min at room temperature; hydrochloric acid (10 M:50 ml, 0.5 mole) was added and stirring was continued for 20 h. The solid was filtered off and triturated with aqueous sodium bicarbonate (1 M; 25 ml) and chloroform (2×25 ml) to leave the title compound as a friable beige solid (1.9 g).

(b)
5-[2-[[2-(2,6-Dimethylphenoxy)-1-methylethyl]amino]-1-hydroxyethyl]thiophene-3-carboxamide Sodium cyanoborohydride (0.7 g) was added portionwise to an ice-cold, stirred, turbid solution of the ethanolamine (1.86 g) and (2,6-dimethylphenoxy)-2-propanone (1.8 g) in methanol (50 ml), water (15 ml) and acetic acid (0.7 ml). The reaction mixture was stirred for 18 h at room temperature, treated with hydrochloric acid (10 M; 5 ml), and stirred for a further 4 h. The resulting solution was basified with aqueous sodium bicarbonate (1 M) and extracted with ethyl acetate (3×80 ml). Evaporation of the dried (MgSO₄) extract gave a yellow semi-solid (3.6 g) which was purified on a silica (Merck 7734; 40 g) column eluted with ethyl acetate/10% methanol/1% ammonia. The appropriate fractions were combined and evaporated to leave a colourless gum, which on trituration with dry diethyl ether (ca. 10 ml) gave the title compound as a white solid (0.26 g) mp 125°-137°. TLC SiO₂ (EtOAc/10% MeOH/1%NH₃ aq) R$_f$0.18.

EXAMPLE 10

5-[2-[[3-(1,3-Benzodioxol-5-yl)-1-methylpropyl]amino]-1-hydroxyethyl]thiophene-3-carboxamide Sodium cyanoborohydride (0.85 g) was added portionwise to an ice-cold, stirred mixture of 5-(2-amino-1-hydroxyethyl)thiophene-3-carboxamide (1.86 g) and (1,3-benzodioxol-5-yl)-2-propanone (1.92 g) in methanol (50 ml), water (15 ml), and acetic acid (0.7 ml). After 24 h, hydrochloric acid (10 M; 5 ml) was added and stirring was continued for 1 h. The reaction mixture was basified with aqueous sodium bicarbonate (1 M) and extracted with ethyl acetate (3×80 ml). Evaporation of the dried (MgSO₄) extract gave a pale brown gum which was triturated with ethyl acetate (50 ml); the residue was further extracted (Soxhlet) with ethyl acetate and the combined organic extracts were evaporated to leave a colourless gum (2.9 g). This was purified on a column of silica (Merck 7734; 60 g) eluted with ethyl acetate/20% methanol/1% ammonia to give on evaporation, the title compound (0.45 g) as a white solid, m.p. 112°-114°. TLC SiO₂ (EtOAc/20% MeOH/1% NH₃ aq.) R$_f$0.28.

EXAMPLE 11

5-[2-[[3-[(1,1'-Biphenyl)-4yl)]-1-methylpropyl]amino]-1-hydroxyethyl]thiophene-3-carboxamide, compound with water (1:1.2)

Sodium cyanoborohydride (0.85 g) was added to an ice cold mixture of 5-[2-amino-1-hydroxyethyl]thiophene-3-carboxamide (1.9 g) and 4-[(1,1'-biphenyl)-4-yl]-2-butanone (2.24 g) in methanol (50 ml), water (15 ml) and acetic acid (0.7 ml). The reaction mixture was stirred for 25 h at room temperature, treated with hydrochloric acid (10 M,5 ml), stirred for a further 1 h, basified with aqueous sodium bicarbonate (2 M; 75 ml), and extracted with ethyl acetate (4×200 ml). The extract was washed with brine (100 ml), dried (MgSO₄) and evaporated to small volume (ca. 40 ml) to precipitate a white solid (A; 0.8 g) which was filtered off and washed with ethyl acetate (10 ml). The filtrate was evaporated to give a sticky white solid which was triturated with dry diethyl ether (ca. 50 ml) to give after filtration a white solid (B; 0.7 g). Further evaporation of the filtrate gave another white solid which was triturated with dry diethyl ether to give an off white solid (C; 0.09 g). The three crude products (A, B and C) were combined, applied on sand to a column of silica (Kieselgel 60; 50 g) eluted with ethyl acetate/18% methanol/2% triethylamine to give a sticky white solid (0.46 g) which on triturition with dry diethyl ether/10% ethyl acetate gave the title compound as a white solid (0.22 g) m.p. 147°-152°. TLC SiO₂ (EtOAc/18%MeOH/2%Et₃N) R$_f$0.32.

EXAMPLE 12

5-[2-[[3-[4-(Dimethylamino)phenyl]-1-methylpropyl]amino-1-hydroxyethyl]thiophene-3-carboxamide Sodium cyanoborohydride (0.96 g) was added to an ice-cold mixture of 5-[2-amino-1-hydroxyethyl]thiophene-3-carboxamide (2.0 g) and 4-[4-(dimethylamino)-phenyl]-2-butanone (1.91 g) in methanol (50 ml), water (15 ml) and acetic acid (0.9 g). The reaction mixture was stirred for 45 h at room temperature, cooled (0°), treated with hydrochloric acid (10 M; 5 ml, 0.05 mol), stirred for a further 1 h, basified with aqueous sodium bicarbonate (2 M; 75 ml), and extracted with ethyl acetate (4×200 ml). The extract was washed with brine (1×200 ml), dried (MgSO$_4$), and evaporated to give a brown oil (ca. 3 g) which was triturated with dry diethyl ether (250 ml) to give a white solid (1.2 g). This was partitioned between aqueous citric acid (4 M; 50 ml) and chloroform (2×50 ml), and the aqueous phase was neutralised with sodium bicarbonate and extracted with ethyl acetate (3×200 ml). The dried (MgSO$_4$) extract was evaporated to give a yellow foam (1.0 g) which was separated on a column of silica (Kieselgel 60; 50 g) eluted with chloroform/9% methanol/1% ammonia (s.g. 0.88) to give an off-white solid (0.48 g) which, on trituration with dry diethyl ether, gave the title compound as a white solid (0.31 g) m.p. 118°–121°. TLC SiO$_2$ (CHCl$_3$/9% MeOH/1% NH$_3$aq) R$_f$ 0.21.

EXAMPLE 13

5-[1-Hydroxy-2-[[1-methyl-2-(methylphenylamino)ethyl]amino]ethyl]thiophene-3-carboxamide, compound with citric acid and water (1:1:0.5)

Sodium cyanoborohydride (0.85) was added to an ice-cold mixture of 5-[2-amino-1-hydroxyethyl]thiophene-3-carboxamide (2.0 g) and 1-[methylphenylamino]-2-propane (1.65 g) in methanol (50 ml), water (15 ml) and acetic acid (0.7 ml). The reaction was stirred for 25 h at room temperature, cooled (0°), treated with hydrochloric acid (10 M; 5 ml) and stirred for a further 1 h. The resulting mixture was extracted with ethyl acetate (4×200 ml); the extract was washed with brine (1×100 ml), dried (MgSO$_4$) and evaporated to small volume (ca. 3.0 ml), and the off-white precipitate (A, 0.9 g) was filtered off. The filtrate was evaporated to give a light brown oil (2.0 g) which was triturated with dry diethyl ether to give an off-white solid (B, 0.2 g). The crude products A and B were combined, applied on silica (MFC, 60–120 mesh) to a short path column of silica (7736H; 200 g) eluted with ethyl acetate/18% methanol/3% triethylamine to give a brown foam (0.2 g) which was dissolved in ethyl acetate (5 ml) and treated with ethereal citric acid to precipitate the title compound as a white solid (0.2 g) m.p. 96°–100°. TLC (Base) SiO$_2$ (EtOAc/18% MeOH/3% Et$_3$N) R$_f$ 0.19.

EXAMPLE 14

5-[1-Hydroxy-2-[(1-methyl-3-phenylpropyl)amino]propyl]thiophene-3-carboxamide hydrochloride (a) 5-(1-Oxopropyl)thiophene-3-carboxamide An ice cold solution of aluminium chloride (13.3 g) in propionyl chloride (40 ml) was stirred for 1 h and thiophene-3-carboxamide (2.54 g) was added. The resulting solution was stirred at 0° for 2 h and at room temperature for 1 h, and poured onto ice (150 g). The white precipitate (1.7 g) was collected and the filtrate was basified with sodium bicarbonate, filtered and extracted with ethyl acetate (3×500 ml). The dried (MgSO$_4$) extract was evaporated to dryness to yield a white solid (2.2 g). The precipitated white material and extracted white material were combined and recrystallised from water to give the title compound as long flat needles (3.1 g) m.p. 145°–148°. TLC SiO$_2$ (EtOAc) R$_f$ 0.28.

(b) 5-(2-Bromo-1-oxopropyl)thiophene-3-carboxamide

A solution of bromine (1.75 ml) in chloroform (100 ml) was added dropwise to a refluxing solution of 5-(1-oxopropyl)-3-thiophenecarboxamide (6.25 g) in chloroform (500 ml) and hydrobromic acid in acetic acid (3 drops) over ca. 2 h. The resulting solution was cooled and evaporated to give an off-white solid (8.87 g) which was partitioned between ethyl acetate (2×300 ml) and sodium bicarbonate (8%, 2×100 ml). The organic phase was washed with water (100 ml), dried (MgSO$_4$), and evaporated to give a light yellow oil which on trituration with chloroform yielded the title compound as a fine white solid (7.35 g) m.p. 116°–117°. TLC SiO$_2$ (EtOAc) R$_f$ 0.33.

(c) 5-[2-[(1-Methyl-3-phenylpropyl)imino]-1-oxopropyl]thiophene-3-carboxamide

A solution of 1-methyl-3-phenylpropylamine (9.0 g) and 5-(2-bromo-1-oxopropyl)thiophene-3-carboxamide (7.6 g) was stirred for 2 h; butanone (75 ml) was added and stirring continued for 48 h. The resulting mixture was filtered and the filtrate evaporated to small volume (ca. 30 ml) and added to vigorously stirred light petroleum (b.p. 60°–80°: 500 ml) to precipitate a yellow gum (ca. 9 g) which was separated on a short path silica (7736H; 300 g) column eluted with ethyl acetate/2% isopropanol/20% triethylamine to give three products. TLC SiO$_2$ (EtOAc/20% i-PrOH/2% Et$_3$N) R$_f$ 0.26, 0.39 and 0.5 respectively.

The compound R$_f$ 0.5 recrystallised from ethyl acetate as a white solid (0.9 g) and was identified by its n.m.r. spectrum as the title compound.

Found: C, 65.8; H, 6.1; N, 8.5; C$_{18}$H$_{20}$N$_2$O$_2$S requires: C, 65.8; H, 6.1; N, 8.5%.

(d) 5-[1-Hydroxy-2-[(1-methyl-3-phenylpropyl)amino]propyl]thiophene-3-carboxamide hydrochloride An ice-cold solution of 5-[2-[(1-methyl-3-phenylpropyl)imino]-1-oxopropyl]thiophene-3-carboxamide (0.7 g) in methanol (50 ml) was treated portionwise with sodium borohydride (0.76 g), stirred at 0° for 1 h, poured onto ice, acidified with dilute hydrochloric acid (2 N), neutralised with aqueous sodium bicarbonate (8%), and extracted with ethyl acetate (2×300 ml). The extract was washed with brine (50 ml) and evaporated to a small volume (ca. 20 ml) to deposit a fine white solid (0.47 g) which was partitioned between ethyl acetate (2×300 ml) and aqueous sodium bicarbonate (1 M; 100 ml). The organic solution (MgSO$_4$) was dried and evaporated to give an off-white foam which was dissolved in ethyl acetate (ca. 100 ml) and treated with ethereal hydrogen chloride to precipitate the title compound (0.42 g) m.p. 125°–130°. TLC SiO$_2$ (3% Et$_3$N/20% i-PrOH/EtOAc) R$_f$ 0.22 and 0.27.

EXAMPLE 15

5-[1-Hydroxy-2-[[2-(4-methoxyphenyl)-1-methylethyl]amino]ethyl]thiophene-3-carboxamide (a) Methyl 5-[1-hydroxy-2-[[2-(4-methoxyphenyl)-1-methylethyl](phenylmethyl)amino]ethyl]thiophene-2-carboxylate Sodium borohydride (3.14 g) was added to an ice-cold suspension of methyl 5-(bromoacetyl)thiophene-2-carboxylate (4.14 g) in methanol (250 ml). After 15 min the reaction mixture was poured into iced water (1000 ml) and extracted with ethyl acetate (5×200 ml). The dried (MgSO4) organic phase was evaporated to give a yellow oil, which was heted with [2-(4-methoxyphenyl)-1-methylethyl](phenylmethyl)amine (5.18 g) at 100° for 16 h. The cooled reaction mixture was partitioned between water (400 ml) and ethyl acetate (3×400 ml), and the dried (MgSO4) organic phase was evaporated, giving the crude product as an oily brown solid (9.75 g). This was applied on silica to a short-path silica column (1000 g) eluted with cyclohexane 15% diethyl ether. The appropriate fractions ($R_f$ 0.15) were combined and evaporated to give the ethanolamine (slightly impure) as an oily beige solid (2.4 g). TLC $SiO_2$ ($Et_2O$/cyclohexane, 1:1) $R_f$ 0.39.

(b) Methyl 5-[1-hydroxy-2-[[2-(4-methoxyphenyl)-1-methylethyl]amino]ethyl]thiophene-2-carboxylate A solution of the benzylated amine (2.4 g) in ethanol (400 ml) and acetic acid (8 ml) was hydrogenated for 24 h over pre-reduced 5% palladium on charcoal (Engelhard 4573; 4 g). The catalyst was filtered off, and the filtrate evaporated to give a viscous yellow liquid, which was partitioned between ethyl acetate (2×50 ml) and aqueous sodium bicarbonate (1 M; 100 ml). The dried (MgSO4) organic phase was evaporated to give a pale brown solid (1 g), which was purified on a silica column (20 g), eluted with ethyl acetate/2% aqueous ammonia/1% methanol. The appropriate fractions were combined and evaporated to give a beige gum, which was triturated with diethyl ether (5 ml) to give an off-white solid (0.78 g) m.p. 88°–90°, which was the desired ester associated with 0.8 mol of acetamide. TLC $SiO_2$ (EtOAc/20% MeOH/1% $NH_3$ aq) $R_f$ 0.57.

(c) 5-[1-Hydroxy-2-[[2-(4-methoxyphenyl)-1-methylethyl]amino]ethyl]thiophene-2-carboxamide A solution of the methyl ester (0.4 g) and aqueous ammonium hydroxide (s.g. 0.88; 80 ml) in methanol (40 ml) was left at room temperature for 72 h and evaporated under reduced pressure. The residual gum was dissolved in hydrochloric acid (2 N; 50 ml), basified with sodium bicarbonate solution (2 N: 50 ml) and extracted with ethyl acetate (3×150 ml). The extract was evaporated and the residual yellow gum triturated with diethyl ether (10 ml) and ethyl acetate (10 ml) to give the title compound as an off white solid (0.28 g) mp 176°–177°. TLC $SiO_2$ (EtOAc/20% MeOH/1% $NH_3$ aq) $R_f$ 0.42.

Pharmaceutical Examples

Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
|---|---|
| Active ingredient | 100.00 |
| Microcrystalline Cellulose B.P.C. | 198.50 |
| Magnesium Stearate | 1.50 |
| Compression weight | 300.00 |

The active ingredient is sieved through a 250 μm sieve, blended with the excipients and compressed using 9.5 mm punches. Tablets of other strengths may be prepared by altering the compression weight and using punches to suit.

| B. Wet Granulation | mg/tablet |
|---|---|
| Active Ingredient | 100.00 |
| Lactose B.P. | 153.50 |
| Starch B.P. | 30.00 |
| Pregelatinised Maize Starch B.P. | 15.00 |
| Magnesium Stearate B.P. | 1.50 |
| Compression weight | 300.00 |

The active ingredient is sieved through a 250 μm sieve and blended with the lactose, starch and pregelatinised starch. The mixed powders are moistened with purified water, granules are made, dried, screened and blended with the Magnesium Stearate. The lubricated granules are compressed into tablets as described for the direct compression formula.

The tablets may be film coated with suitable film forming materials, e.g. methyl cellulose or hydroxypropyl methyl cellulose using standard techniques. Alternatively the tablets may be sugar coated.

| Capsules | mg/capsule |
|---|---|
| Active ingredient | 100.00 |
| *STA-RX 1500 | 49.25 |
| Magnesium Stearate B.P. | 0.75 |
| Fill weight | 150.00 |

*A form of directly compressible starch supplied by Colorcon Ltd., Orpington, Kent.

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| Sustained Release Tablets | mg/tablet |
|---|---|
| Active ingredient | 300.00 |
| *Cutina H.R. | 60.00 |
| Lactose B.P. | 137.50 |
| Magnesium stearate B.P. | 2.50 |
| Compression weight | 500.00 |

The active ingredient is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 12.0 mm punches to produce tablets with a hardness of not less than 10 Kp (Schleuniger tester).

| Syrup | mg/5ml dose |
|---|---|
| Active ingredient | 100.00 mg |
| Sucrose B.P. | 2750.00 |
| Glycerine B.P. | 500.00 |
| Buffer | |
| Flavour | |
| Colour | As required |
| Preservative | |

| Syrup | mg/5ml dose |
| --- | --- |
| Distilled water | 5.00 ml |

The active ingredient, buffer, flavour, colour and preservative are dissolved in some of the water, and the glycerine is added. The remainder of the water is heated to 80° and the sucrose is dissolved in this and cooled. The two solutions are combined, adjusted to volume and mixed. The syrup produced is clarified by filtration.

| Injection for Intravenous administration | % w/v |
| --- | --- |
| Active ingredient | 1.00 |
| Water for injections B.P. to | 100.00 |

Sodium chloride may be added to adjust the tonicity of the solution and the pH may be adjusted to that of maximum stability using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Eye Drops | % w/v |
| --- | --- |
| Active ingredient | 0.5 |
| Preservative | As required |
| Distilled water | 100.00 |

Sodium chloride or other suitable salts may be added to adjust the tonicity of the solution and buffers may be used to adjust the pH to that of maximum stability.

The solution is prepared, clarified and filled into appropriate containers which are then closed to exclude micro-organisms and sterilised by heating in an autoclave using one of the acceptable cycles. Alternatively the solution may be sterilised by filtration and filled into sterile containers under aseptic conditions. The solution may be packed under an inert atmosphere of nitrogen.

We claim:

1. A compound of general formula (I):

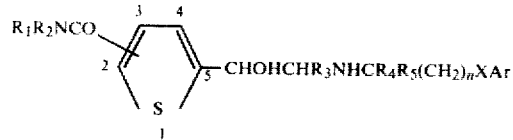

in which the amide function is in the 2 or 3 position on the thiophene ring, and wherein $R_1$, $R_2$, $R_3$, $R_4$ and $R_5$, which may be the same or different, each represents a hydrogen atom or a lower alkyl group;

X represents $-CH_2-$, $-O-$ or $-NR_6-$ where $R_6$ represents a hydrogen atom or a lower alkyl group;

n is a number from zero to 3 with the proviso that when n is zero X can not represent $-O-$ or $-NR_6-$;

Ar represents a phenyl group optionally substuted by one or more substituents selected from halogen atoms, $C_1-C_3$ alkyl groups, phenyl groups and the groups $-OR_7$ or amino groups ($-NR_8R_9$) in which $R_7$ and $R_8$ and $R_9$ independently represent a hydrogen atom or a $C_1-C_3$ alkyl group or an alkylenedioxy group of formula $-O(CH_2)_mO-$ where m is 1 or 2 and physiologically acceptable salts thereof.

2. A compound according to claim 1, wherein the groups represented by $R_1$ to $R_6$ inclusive are hydrogen atoms or methyl groups.

3. A compound according to claim 1, wherein n is 1.

4. A compound according to any of claims 1 to 3, wherein X is $-CH_2-$.

5. A compound according to any of claims 1 to 3, wherein Ar represents a phenyl group or a phenyl group substituted by a fluorine atom, or a dimethylamino, phenyl or methylenedioxy group.

6. 5-[1-Hydroxy-2-[(1-methyl-3-phenylpropyl)amino]ethyl]thiophene-3-carboxamide.

7. A compound according to claim 2 wherein n is 1.

8. A compound according to claim 4 wherein Ar represents a phenyl group or a phenyl group substituted by a fluorine atom, or a dimethylamino, phenyl or methylenedioxy group.

9. A pharmaceutical composition comprising as active ingredient at least one compound according to any of claim 1, together with one or more physiologically acceptable carriers or excipients.

10. A pharmaceutical composition according to claim 9 which is formulated in unit dosage form and which contains from 5 mg to 800 mg of the active ingredient.

11. A method for the treatment of a patient suffering from a cardiovascular disorder which comprises administering to the patient an effective amount of a compound according to claim 1.

12. A method for the treatment of a patient suffering from glaucoma or a peripheral vascular disease which comprises administering to the patient an effective amount of a compound according to claim 1.

13. A pharmaceutical composition comprising as active ingredient at least one compound according to claim 4 together with one or more physiologically acceptable carriers or excipients.

14. A pharmaceutical composition comprising as active ingredient at least one compound according to claim 5 together with one or more physiologically acceptable carriers or excipients.

15. A pharmaceutical compositon according to claim 13 which is formulated in unit dosage form and which contains from 5 mg to 800 mg of the active ingredient.

16. A pharmaceutical composition according to claim 14 which is formulated in unit dosage form and which contains from 5 mg to 800 mg of the active ingredient.

* * * * *